United States Patent [19]
Park

[11] Patent Number: 6,017,517
[45] Date of Patent: Jan. 25, 2000

[54] METHOD FOR TREATING HUMAN NAILS

[75] Inventor: Debra A. Park, Mesa, Ariz.

[73] Assignee: The Dial Corporation, Scottsdale, Ariz.

[21] Appl. No.: 08/984,580

[22] Filed: Dec. 3, 1997

Related U.S. Application Data

[60] Provisional application No. 60/033,118, Dec. 18, 1996.

[51] Int. Cl.[7] ............................ A61K 7/00; A61K 7/04
[52] U.S. Cl. ............................... 424/61; 424/401
[58] Field of Search ................... 424/61, 78.02, 424/70.19, 70.22, 401; 514/844, 846, 873, 973, 975

[56] References Cited

U.S. PATENT DOCUMENTS

| | | | |
|---|---|---|---|
| Re. 33,845 | 3/1992 | Schreuder | 424/59 |
| 3,034,965 | 5/1962 | Drake et al. | 167/85 |
| 3,992,519 | 11/1976 | Hofmann et al. | 424/48 |
| 4,158,053 | 6/1979 | Greene et al. | 424/61 |
| 4,402,935 | 9/1983 | Gordon et al. | 424/61 |
| 4,416,873 | 11/1983 | Puchalski et al. | 424/177 |
| 4,478,853 | 10/1984 | Chaussee | 424/358 |
| 4,482,537 | 11/1984 | El-Menshawy et al. | 424/59 |
| 4,534,964 | 8/1985 | Herstein et al. | 424/70 |
| 4,595,586 | 6/1986 | Flom | 424/59 |
| 4,690,818 | 9/1987 | Puhalski et al. | 424/70 |
| 4,721,705 | 1/1988 | Shreuder | 514/54 |
| 4,832,872 | 5/1989 | Scandel | 252/547 |
| 4,851,434 | 7/1989 | Dekner | 514/847 |
| 4,857,321 | 8/1989 | Thomas | 424/95 |
| 4,863,725 | 9/1989 | Deckner et al. | 424/81 |
| 4,897,261 | 1/1990 | Yamazaki et al. | 424/61 |
| 4,970,220 | 11/1990 | Chaussee | 514/358 |
| 5,041,285 | 8/1991 | Lundmark | 424/70 |
| 5,069,898 | 12/1991 | Goldberg | 424/70 |
| 5,102,654 | 4/1992 | Castrogiovanni et al. | 424/61 |
| 5,136,093 | 8/1992 | Smith | 564/197 |
| 5,425,954 | 6/1995 | Thompson et al. | 424/401 |
| 5,439,682 | 8/1995 | Wivell et al. | 724/401 |
| 5,445,823 | 8/1995 | Hall et al. | 424/401 |
| 5,599,549 | 2/1997 | Wivell et al. | 424/401 |
| 5,720,961 | 2/1998 | Fowler et al. | 424/401 |

OTHER PUBLICATIONS

"Panthenol—The Beautifying Vitamin—The Rationale for its use in Hair, Skin & Nail Care Products", Hoffmann–La Roche Inc.

"Panthenol—Effects on Fingernail Properties", Hoffmann–La Roche Inc.

"Panthenol—Nail Flexibility Study", Hoffmann–La Roche Inc.

*Primary Examiner*—Thurman K. Page
*Assistant Examiner*—Sharon Howard
*Attorney, Agent, or Firm*—Richard G. Harrer

[57] ABSTRACT

A method for improving the flexibility of human fingernails by washing the hands in a normal fashion with a cleansing composition containing at least about 0.5% by weight of panthenol for at least about three (3) times per day and for at least about three (3) times per day and for at least about three (3) consecutive days, with each washing being followed by rinsing the hands with water.

10 Claims, No Drawings

METHOD FOR TREATING HUMAN NAILS

This application claims benefit of provisional application 60/033118, filed Dec. 18, 1996.

This invention relates to methods and compositions for improving the physiology of human nails. More particularly, the invention is directed to methods for improving the condition of human nails by washing the hands in a normal manner using a skin cleansing composition containing panthenol. The invention also includes skin cleansing compositions incorporating panthenol which accomplish the improvement in the condition of human nails.

BACKGROUND OF THE INVENTION

The nail plate is a hard keratinous structure. Its horny cells are cemented together tightly and do not separate, as do stratum corneum cells. Thus, nails can extend indefinitely unless cut or broken. A variety of nail changes can occur in response to systemic and external stresses. For example, prolonged fevers, drug reactions, chemical toxemia and malnutrition may cause the nails to shed altogether, or there may be various degrees of thinning, splitting, ridging or furrowing of the nails. Even emotional stresses may be reflected in abnormal nails. Harsh environmental conditions can cause nails to crack or to become brittle and crack; also, even the use of nail enamel removers can have an adverse effect on the nails. Furthermore, fragile, brittle, thinned or split nails can occur, even in the absence of any discernible abuse.

Over the years, the cosmetic industry has developed and marketed numerous nail treatment products compounded with protein derivatives which are claimed to alleviate the problem of nail brittleness and breakage effecting a large number of women who maintain long nails. U.S. Pat. Nos. 4,402,935; 3,034,965; 4,158,053 and 4,897,261 are all directed to nail treatment products which are applied to the nails and left in place. In U.S. Pat. No. 5,102,654, a nail enamel emulsion composition containing a water phase and a lacquer phase is disclosed. This patent also discloses that vitamins such as panthenol can be incorporated in the product as an optional additive. If used, the panthenol is employed in an amount ranging from about 0.001–0.015 w/w %.

Panthenol, which is an alcohol corresponding to panthothenic acid with vitamin activity, conforms to the formula:

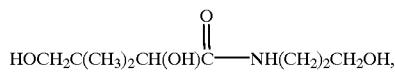

has been used rather extensively in hair and skin products for a number of years. For example, U.S. Pat. No. 5,069,898 discloses a hair enrichment composition which contains from 0.005 to 15 weight percent of a hair bulking agent which could include panthenol, biotin, a mucopolysaccharide or mixtures thereof. U.S. Pat. No. 5,445,823 discloses a dermatological composition which contains some panthenol to reduce the skin irritation associated with use of benzoyl peroxide. U.S. Pat. No. 5,425,954 discloses a product which contains panthenol for treating psoriasis. Other patents showing use of panthenol in skin products are U.S. Pat. Nos. 4,721,705; 4,783,332; 5,041,285; 4,595,586; 4,478,853; 4,416,873; 4,863,725; 4,857,321; 4,851,434, and 4,482,537.

There is unpublished information from a supplier of panthenol that panthenol is a useful ingredient in skin care products, particularly hair care products. This information also notes the role of panthenol in nail care products and indicates that when used in a particular manner, it is absorbed into nails and imparts flexibility. This information also includes a report on a study in which a panel of eleven people were subjected to a 0.5% dl-panthenol solution for five days. More specifically, the thumb and third finger of the hand of each person was immersed in the solution to cover the nails for five minutes. This was repeated for five days. The "physiolastic" characteristic of the nails was measured three hours after treatment, and it was concluded that there was a trend for both the rigidity modulus and the viscosity of fingernails to increase after treatment with this solution. Also, this information included a study utilizing nail fragments. In this study, nail flexibility was determined after soaking the fragments in water only. Other nail fragments were soaked in test solutions for 15 minutes, rinsed with water and blotted dry. This was repeated 20 times. The study seemed to show that a solution of 1% panthenol and 1% Triton X-100 improved nail flexibility.

SUMMARY OF THE INVENTION

This invention is directed to a method for improving the physiology of human nails and, more particularly, improving the flexibility of nails by washing the hands with a cleansing composition containing panthenol. The method entails washing the hands with the cleansing composition in a normal fashion; that is, the user thoroughly washes his/her hands, followed by rinsing with water. Initial studies indicate that washing the hands three times per day for at least three days, and preferably at least five days using a level of panthenol in the cleansing product of at least about 0.5% or more will result in a measurable improvement in nail flexibility. The cleansing composition may be in liquid or solid form and contain a relatively mild surfactant, along with other known skin benefiting agents.

DETAILED DESCRIPTION OF THE INVENTION

This invention relates to a method of improving the physiology of human nails, particularly to improving the flexibility of such nails, by washing the hands with a cleansing composition containing panthenol. The method entails washing the hands with the cleansing composition in a normal fashion; that is, the user thoroughly washes his or her hands, followed by thorough rinsing with water. It is preferred that the washing operation take place at least three times per day for at least three days and preferably five days, with a level of panthenol of at least 0.5% by weight or more of the cleansing composition. Such a method will result in a measurable improvement in nail flexibility.

Panthenol, is an alcohol corresponding to panthothenic acid with vitamin activity, and conforms to the formula:

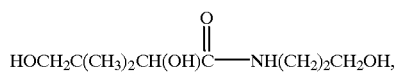

and is also known as 2,4-Dilydroxy-N-(3-Hydroxypropyl)-3,3-Di-methylbutanamide, and is available in the dextro ("d") and dextro and levo ("dl") forms, the latter being preferable. The level of panthenol which is useful in this invention is from about 0.5% to about 1.5% by weight of the composition, with about 1% by weight being preferable.

The cleansing composition may be in liquid or solid form with the liquid being preferred. In a liquid form, the surfactant employed should comprise from about 5% to about 25% by weight of the composition, with from about 7% to 15% by weight being preferred. Since the cleansing composition is for use on the skin, the surfactant should be relatively mild, and a variety of these are well known in the art. Preferably, a mild anionic surfactant is used and can include sulfates such as sodium laureth sulfate and ammonium lauryl sulfate, long chain ($C_8$–$C_{22}$) acylisethionates, and alkyl glycerol ether sulfonates having 8–22 carbons, preferably 10–18 carbons. Additives that may be included are amides, such as cocamide DEA, and a variety of skin benefiting agents such as hydrolyzed animal protein and the like. Moisturizers may also be included to provide additional skin conditioning benefits and help with the mildness of the product.

In solid form, the cleansing composition is preferably a soap bar which is formed from the well-known alkali metal salts of fatty acids having alkyl chain lengths of $C_8$–$C_{22}$, preferably $C_{12}$–$C_{18}$. For example, sodium tallowate, sodium palm kernalate, or sodium cocoate and mixtures thereof perform very well. The fatty acid soaps can be present in amounts up to about 90% by weight of the composition, preferably in the range of 60–80% by weight, and most preferably in the range of about 65–70% by weight. Such cleansing compositions formed of soap will additionally contain lathering agents, moisturizing agents, and the like, all of which are very well known in the art. The cleansing composition in bar form, such as alkyl glycerol sulfanates plus alkyoly (ACYL) sarcosinates and the like. Such synthetics surfactants are used at levels up to about 70% by weight of the bar. Additional surfactants that may be employed include ACYL isethionates, alkyoly sulfosucinates, aminoxides, betaines, sultains, and mixtures thereof.

EXAMPLE I

A liquid cleansing composition suitable for hand washing was prepared having the following ingredients:

| Ingredient | Blended Wt % | Actual Wt % |
|---|---|---|
| Water | 61.60 | 87.67 |
| Citric Acid (anhydrous) | 0.10 | 0.10 |
| Sodium Laureth Sulfate | 25.00 (25% active) | 6.3 |
| Ammonium Lauryl Sulfate | 5.00 (30% avtive) | 1.5 |
| Cocamide DBA | 2.00 | 2.00 |
| Cocamidopropyl Betaine | 5.00 (35% active) | 1.8 |
| Polyquaternium 7 | 0.50 (8% active) | 0.04 |
| DMDM Hydantoin | 0.40 (55% active) | 0.22 |
| Tetrasodium BDTA | 0.05 (40% active) | 0.02 |
| Sodium Chloride | 0.35 | 0.35 |

In preparing this composition, the water was heated to about 95° and the ingredients were added in the order as shown with constant mixing, particularly after the addition of the amide The pH was adjusted to between 5.8 and 6.6.

This batch was then divided into three (3) equal portions designated A, B and C. Sufficient dl panthenol was added to portion A so that it contained 0.5% by weight of panthenol. Sufficient dl panthenol was added to portion B so that it contained 1.0% by weight of the panthenol. Portion C contained no panthenol.

EXAMPLE II

The procedure for evaluating the ability of the A, B and C compositions to improve nail flexibility is as follows:

Three (3) panels of five (5) female subjects each of age 40 years or older were selected. All subjects had long nails with nail length of at least 3/4 cm from root. All subjects were refrained from using any nail product for one week prior to the initiation of the study. Each panel was assigned an A, B or C composition and subjects were instructed to wash their hands with the respective composition three time per day. The quantity of composition used during each hand washing was standardized. Hand washing included 2 minutes of foaming, followed by thorough rinsing with water. On days 0, 3 and 5, nail flexibility measurements were obtained on nails of the middle fingers of subjects using the instrument as shown in FIG. 1.

In vivo nail flexibility can be accurately measured using the instrument shown in FIG. 1. As shown, the hand is positioned on a platform with the middle finger positioned over an edge of the platform. The end of the finger is supported on a horizontal extension of the platform with the nail extending downwardly from the extension. The load cell probe is moved to a preselected spot near the tip of the finger nail using the micrometer to position the probe. The probe is then moved away from the nail using the moving motor and then slowly moved toward the nail and ultimately to indent the nail. The force required for indentation and distance traveled by the probe were recorded. All results were recorded as force/distance or gm/mm.

The results of the use of compositions A, B and C on nail flexibility are summarized in Tables 1, 2 and 3 which follow.

TABLE 1

EFFECTS OF LIQUID HAND SOAP TREATMENT ON NAIL FLEXIBILITY
Treatment with Composition C (0% DL-Panthenol)

| | Nail Flexibility (gm/mm) | | |
|---|---|---|---|
| Subject # | DAY 0 | DAY 3 | DAY 5 |
| 1 | 89.2* | 94.3 | 86.7 |
| 2 | 134.5 | 127.5 | 131.5 |
| 3 | 151.3 | 132.6 | 155.7 |
| 4 | 103.7 | 108.4 | 110.3 |
| 5 | 142.8 | 151.3 | 145.8 |
| Average | 124.3 ± 26.6 | 122.8 ± 22.1 | 126.0 ± 27.8 |
| % Change | | 1.2% | −1.4% |

*Average of three measurements

TABLE 2

EFFECTS OF LIQUID HAND SOAP TREATMENT ON NAIL FLEXIBILITY
Treatment with Composition A (0.5% DL-Panthenol)

| | Nail Flexibility (gm/mm) | | |
|---|---|---|---|
| Subject # | DAY 0 | DAY 3 | DAY 5 |
| 1 | 137.6* | 148.2 | 139.7 |
| 2 | 192.5 | 181.4 | 180.3 |
| 3 | 126.5 | 130.6 | 127.4 |
| 4 | 110.7 | 102.6 | 103.3 |
| 5 | 147.6 | 149.2 | 150.4 |
| Average | 143.0 ± 31.0 | 142.4 ± 25.8 | 140.2 ± 25.5 |
| % Change | | 0.4% | 2.0% |

*Average of three measurements

TABLE 3

EFFECTS OF LIQUID HAND SOAP TREATMENT ON
NAIL FLEXIBILITY
Treatment with Composition B (1.0% DL-Panthenol)

| | Nail Flexibility (gm/mm) | | |
|---|---|---|---|
| Subject # | DAY 0 | DAY 3 | DAY 5 |
| 1 | 164.2* | 151.3 | 141.2 |
| 2 | 109.5 | 106.4 | 101.3 |
| 3 | 151.3 | 132.5 | 123.6 |
| 4 | 132.6 | 141.7 | 136.2 |
| 5 | 93.5 | 90.3 | 81.2 |
| Average | 130.3 ± 29.0 | 124.4 ± 25.4 | 116.7 ± 25.1 |
| % Change | | 4.5% | 10.4% |

*Average of three measurements

As the results in Tables 1, 2 and 3 indicate, the average baseline nail flexibility without any treatment ranged from 124 to 143 gm/mm for the three separate panels. After three days of handwashing, washing with Composition B (1.0% dl-panthenol) showed measurable improvement. After five days of treatment, washing with Composition A (0.5% dl panthenol) showed an increase in nail flexibility of 2.5%; using Composition B (1.0% dl panthenol) showed a 10.4% increase in nail flexibility. No increase in nail flexibility was demonstrated using Composition C )0% dl-panthenol).

Clearly, this series of experiments demonstrates that a liquid cleansing composition containing panthenol when used to wash a user's hands in a normal fashion will improve the flexibility of the user's nails after a relatively short period of time.

I claim:

1. A method for improving the flexibility of human fingernails consisting essentially of the steps of washing the hands in a normal fashion with a cleansing composition containing at least about 0.5% by weight of panthenol for at least about 3 times per day and for at least about 3 consecutive days, each of said hand washings being followed by rinsing the hands with water.

2. The method of claim 1 wherein said cleansing composition contains from at least about 0.5% to about 1.5% by weight of panthenol.

3. The method of claim 2 wherein said hand washing takes place for at least for at least about five consecutive days.

4. The method of claim 3 wherein said cleansing composition contains at least about 1.0% by weight of panthenol.

5. The method of claim 4 wherein said cleansing composition is in liquid form and contains from about 5% to about 25% by weight of a mild surfactant.

6. The method of claim 5 wherein said mild surfactant is an anionic surfactant.

7. The method of claim 4 wherein said composition is in solid form.

8. The method of claim 7 wherein said composition contains up to about 90% by weight of a soap or from alkali metal salts of fatty acids having alkyl chain links of $C_8$–$C_{22}$.

9. The method of claim 8 wherein said soap comprises from about 60% to about 80% by weight of such composition and wherein said alkyl chain lengths are from $C_{12}$–$C_{18}$.

10. The method of claim 7 wherein said solid composition contains both soap and a synthetic detergent.

* * * * *

UNITED STATES PATENT AND TRADEMARK OFFICE
CERTIFICATE OF CORRECTION

PATENT NO. : 6,017,517
DATED : January 25, 2000
INVENTOR(S) : Debra A. Park

It is certified that error appears in the above-indentified patent and that said Letters Patent is hereby corrected as shown below:

Title page, item [57] Abstract, the duplicate words "for at least about three (3) times per day" should be deleted.

In column 3, Example I, line 43, the word "DBA" should be deleted and the word -- DEA-- should be inserted; and In column 3, Example I, line 49 the word "BDTA" should be deleted and the word -- EDTA -- should be inserted.

Signed and Sealed this

First Day of May, 2001

Attest:

NICHOLAS P. GODICI

*Attesting Officer*    *Acting Director of the United States Patent and Trademark Office*